United States Patent [19]

Hatano et al.

[11] 4,351,978

[45] Sep. 28, 1982

[54] METHOD FOR THE DISPOSAL OF POLYCHLORINATED BIPHENYLS

[75] Inventors: Yasuhiro Hatano, Sakaishi; Kazumune Nakao, Hyogo, both of Japan

[73] Assignees: Osaka Prefectural Government; Daido Sanso Kabushiki Kaisha, both of Osaka, Japan

[21] Appl. No.: 170,535

[22] Filed: Jul. 21, 1980

Related U.S. Application Data

[63] Continuation-in-part of Ser. No. 80,531, Oct. 1, 1970, abandoned, which is a continuation of Ser. No. 888,530, Mar. 21, 1978, abandoned.

[51] Int. Cl.³ .............................................. C07C 1/20

[52] U.S. Cl. .................................... 585/469; 570/204

[58] Field of Search ......................... 585/469; 570/204

[56] References Cited

U.S. PATENT DOCUMENTS

| | | | |
|---|---|---|---|
| 3,595,931 | 7/1971 | Hay et al. | 585/469 |
| 4,022,795 | 5/1977 | Bamfield et al. | 585/469 |
| 4,144,152 | 3/1979 | Kitchens | 204/158 R |

OTHER PUBLICATIONS

Sewai et al., Chem. Abs. 81, 135262e, (1974).
Shimozaki et al., Chem. Abs. 83, 9446w, (1975).
Sawai et al., Chem. Abs. 85, 112349g, (1976).
Sawai et al., Chem. Abs. 85, 166160g, (1976).

*Primary Examiner*—Curtis R. Davis
*Attorney, Agent, or Firm*—Eyre, Mann, Lucas & Just

[57] ABSTRACT

The invention provides a method of disposing of polychlorinated biphenyls without causing a health hazard to the public in which the polychlorinated biphenyls are converted into harmless and useful compounds. This is accomplished by the hydrogenation-dechlorination thereof.

12 Claims, 2 Drawing Figures

METHOD FOR THE DISPOSAL OF POLYCHLORINATED BIPHENYLS

This application is a continuation-in-part of U.S. application Ser. No. 080,531, filed Oct. 1, 1979, which is a continuation of U.S. application Ser. No. 888,530 filed Mar. 21, 1978, both now abandoned.

The present invention relates to a method of disposing of polychlorinated biphenyls without causing a health hazard to the public. More particularly, the present invention relates to a method of converting polychlorindated biphenyls into useful compounds by the hydrogenation-dechlorination thereof.

It is known in the art that polychlorinated biphenyl (hereinafter referred to as PCB) is a useful substance for example as a transformer oil, a capacitor oil, a heat transfer agent and in carbonless reproducing paper. It has been in wide use for these and other applications. On the other hand, in view of the recent increased public interest in pollution problems, the toxic nature of PCB has also drawn a lot of attention, and the recovery of unused PCB has been started. However, a further problem has been brought about as to how to dispose of it without causing a health hazard to the public. So far, many proposals have been made for disposing of the unused PCB, such as incineration, ultraviolet decomposition, hydrothermal decomposition and radiolysis. However, it has been found that the disposal of it under these methods is not satisfactory. Under the incineration methods it is impossible to consume PCB completely by fire, and additionally, it is likely to cause contamination of the air. Under the ultraviolet decomposition method the biphenyls and sodium chloride constitute a bar to the transmission of ultraviolet rays. The radiolysis methods are effective only when the PCB to be treated is extremely diluted; as a result, they have no practical value. Lastly, under the hydrothermal decomposition methods it is required to conduct them at costly elevated temperatures and high pressure (e.g. at 300° C., 200 atm). Furthermore the products obtained through these methods are not identified, thereby making it uncertain that they can be dumped as sewage.

The present invention aims at overcoming the difficulties of the known methods of disposing of PCB, and has for its object to provide an improved method for the safe disposal of PCB. The invention is based on discovery that PCB can be converted into various useful compounds. The PCB is first emulsified and dispersed in an alkaline aqueous solution. It is then reacted with hydrogen in the presence of a hydrogenation catalyst. It has been discovered that there is obtained not only a rendering harmless of the PCB but also useful compounds are obtained as by-products of the hydrogenation-dechlorination of the PCB.

Therefore, according to the present invention the disposal of PCB includes the steps of emulsifying and dispersing PCB in an alkaline aqueous solution, and reacting the same with added gaseous hydrogen in the presence of hydrogenation catalyst, wherein the sequence of adding alkali, water, an emulsifying-dispersing agent, and PCB is not important if the added PCB is resultantly emulsified and dispersed in the alkaline aqueous solution.

As described above, according to the present invention a great deal of PCB is dechlorinated and converted into various useful compounds, wherein the hydrogen chlorides produced through the reaction of PCB with hydrogen are changed into harmless salts, and wherein the products obtained in this way are separately collected. In addition, according to the present invention there is no need for using high temperatures and high pressures, since the reaction is practicable under normal conditions.

The method of this invention is applicable either to individual PCB compounds or to a mixture thereof.

According to the present invention, PCB is firstly converted into biphenyl as a result of dechlorination through a hydro-dechlorinating reaction, and a part of the biphenyl is converted into bicyclohexyl through hydrogenation. It is also possible to allow the reaction to continue until the whole amount of biphenyl is converted into bicyclohexyl. Depending upon the reaction conditions, it is possible to obtain benzene and any other dechlorinated products.

In this invention it is essential to emulsify and disperse PCB in an alkaline aqueous solution. It has been found that this is essential to enable the PCB to react with hydrogen effectively. The resulting hydrogen chloride reacts with the alkali content in the solution, thereby producing a harmless salt. The reaction takes place in the presence of a hydrogenation catalyst, and in particular a Raney nickel catalyst. It has been found through experiments that a Raney nickel catalyst preferably needs the continuous addition of alkali in order for its activity to last; otherwise the activity will not last. The alkali used for this invention can be selected from known strong bases and are preferably metal hydroxides, such as sodium hydroxide, potassium hydroxide, calcium hydroxide, and lithium hydroxide. The amount of alkali to be used depends upon the amount and type of PCB to be treated; however, it is necessary to use a sufficient amount of alkali to react with the entire amount of hydrogen chloride produced through the reaction of the PCB with hydrogen. It is permissible to use a slightly excessive amount of alkali as compared to the amount of hydrogen chloride.

It has been also found that when the alkali is one normal or less, a better emulsifying and dispersing of PCB will result, whereas when it is so highly concentrated as to exceed one normal the emulsifying and dispersing thereof will decelerate in proportion to the increasing normality, thereby resulting in a retarded reaction. In addition, it has been found that the reaction proceeds smoothly when the equivalent ratio of alkali to PCB ranges from 0.5 to 1.25, preferably from 0.75 to 1.1 (especially in the range of 0.5 to 1.0 the reaction velocity is relatively high until it reaches the point of neutralization). Accordingly the amount of alkali is preferably restricted by that of PCB to be treated, and the amount of PCB also determines the minimum amount of dispersing medium. Furthermore, it has been found that the alkali and the reduction circumstances are effective to protect the reaction chamber, and that irrespective of the high concentration of alkali the Raney nickel catalyst maintained its activity after the reaction was finished. Preferably a suitable emulsifying dispersing agent is used to emulsify and disperse PCB in the alkaline aqueous solution. For this agent a low molecular weight alcohol such as methyl alcohol, ethyl alcohol, isopropyl alcohol, n-propyl alcohol has been found to be effective to disperse PCB in the alkaline aqueous solution. The amount of the agent is not limited, but in the case of, for example, methyl alcohol, it is preferred that 20 to 50 g is used for each 100 g of water. The exact figure, of course, depends upon the number of chlorides contained in the PCB to be treated. These agents can be used singly or in a combination.

In cracking PCB, the ratio of water to the emulsifying-dispersing agent is 0.3 to 4:1, preferably 2:1 so as to secure the minimum amount of dispersing medium. The amount of emulsifying-dispersing agent affects the emulsifying and dispersing of PCB; neither excess nor shortage produces a good result. In making a solution containing a dispersed PCB, it is also possible to use the same amount of emulsifying-dispersing agent as that of water, and in this case it has been found that methyl alcohol makes hydrogen most soluble of the three; then ethyl alcohol; and finally isopropyl alcohol.

The adding ratios of PCB, alkali, emulsifying-dispersing agent, and water are preferably determined such that the solution of 800 to 2000 ml, preferably 900 to 1200 ml, should contain alkali of 0.5 to 1.25 gram equivalent weight (preferably 0.75 to 1.1 gram equivalent weight) and emulsifying-dispersing agent of 100 to 450 ml (preferably 170 to 380 ml) with respect to each gram of chloride contained in the PCB.

For the hydrogenation catalysts for use in this invention known types can be safely selected and used, e.g. Raney catalysts, such as a Raney nickel catalyst, a Raney cobalt catalyst; modified Raney catalysts (which are produced by the addition of lead, antimony, etc. to a nickel-aluminium alloy); platinum, palladium, and rhodium. These catalysts can be used singly or in a combination of two or more. The amount to be used depends upon the type of the catalyst and the reaction conditions, and can be determined in a wide range. For example, a 10% carbon-supported palladium catalyst of 1 to 3 gram can be used with respect to 100 gram of PCB (AC 1254). It has been found that the Raney nickel catalyst is very reactive in the alkaline and neutral zones up to 160° C.

The desired pressures for carrying out this invention range from normal to 100 atm, preferably normal to 30 atm, and they are adjusted in accordance with the pressure of the gaseous hydrogen. It is preferred to use a greater amount of hydrogen than that calculated on principle to be necessary for the hydrogenation reaction. The hydrogenation-dechlorination reaction has been found to be almost independent of pressure, and therefore, the reaction velocity can be considered constant whether the initial pressure is 100 atm or 30 atm. Even if the partial pressure of hydrogen is 1 to 10 $kgw/cm^2$, the reaction proceeds, and its velocity is comparable to when the pressure is high. The method of this invention can be performed at room temperature, but the higher the temperature is, the more the reaction accelerates. However, when the temperatures exceed 200° C. the hydrogenation catalyst, such as especially a Raney catalyst, may lose its activity, and it is therefor preferred to carry out the reaction at a temperature not higher than 200° C., preferably 40° to 160° C., particularly for industrial utilization. The period of time for reaction to complete depends upon the activity of the catalyst, the reaction temperature and other factors, but normally it goes close to total completion in 0.1 to 48 hours.

The viscosity of PCB increases as the average number of chlorine atoms per molecule increases, with a rising pour point, thereby making the same difficult to be emulsified and dispersed in the solution. A decachlorinated biphenyl compound has almost the same fluidity of 160° C. as that of a tetra chlorinated biphenyl at 100° C., so that there is no difficulty for the same to become emulsified and dispersed, thereby enabling the reaction to proceed smoothly. In this case, it has been found that elevation of temperature makes the emulsifying and dispersing develop, and that agitation of the solution also favorably affects the emulsifying and dispersing properties. In the case of the Raney nickel catalyst the practical range of temperatures for the hydrogenation is up to 160° C. in view of the effective continuation of activity. The reaction velocity tends to multiply 2 to 4 times in the range of 70° C. to 200° C. as the temperature rises by 10° C.

A typical example of the operation according to the present invention will be explained:

A hydrogenation catalyst, alkali, water and a dispersing agent are added in a high pressure container, such as an autoclave, in which a PCB is evenly emulsified and dispersed. The gaseous hydrogen is bubbled into the container, and the reaction is effected at the required temperature under the required pressure. After the reaction is finished, the products are separated into each compound by fractional distillation through the utilization of differences in their boiling points.

Alternatively, the following method may be used:

Since the mixture in the container becomes gradually separated into products in the upper portion of the container and an unreacted PCB in the lower portion thereof, the products which are mainly biphenyl when carried out under low pressure in the upper portion are taken out while the reaction is stopped. There following, a fresh supply of PCB is added to the remainder in the container. In this way the reaction resumes in the container, while the products removed are separated into individual compounds by partial distillation.

As a third alternative, the mixture in the container is separated into unreacted PCB and products by distillation in a closed system while the reaction is stopped. This is relatively easy to accomplish because of the remarkably high boiling point of the PCB compared with those of the products formed. The products obtained in this way are separated into individual compounds by distillation.

The present invention will be better understood by the following examples:

EXAMPLE 1

9.0 g of PCB (made by Mitsubishi-Monsanto Co., Ltd.) the average number of chlorine atoms per molecule: 3 (0.105 gram equivalent weight), 4.2 g of sodium hydroxide (0.105 gram equivalent weight), and 20 ml of isopropyl alcohol were admixed. 10 g of powdered Ni-Al alloy (Ni: 50%) was added to the admixture as a catalyst together with water. The powdered Ni-Al alloy had been previously developed at 50° C. for 50 minutes with 45 ml of a 30% solution of sodium hydroxide, until the total amount reached 100 ml. This dispersing solution was added in an autoclave capable of oscillation (with a Nichrome heater, capacity: 250 ml), and gaseous hydrogen was introduced. Then the reaction was effected at 100° C. under about 100 $kgw/cm^2$ of Hg total pressure, wherein the vapor phase was 150 ml. Table 1 shows the relationship among the total pressure of hydrogen in the autoclave, the rate of dechlorination and the reaction time.

TABLE 1

| REACTION TIME (hour) | TOTAL PRESSURE (mainly $H_2$) ($kg/cm^2$) | RATE OF DE-CHLORINATION(*) (%) |
|---|---|---|
| 0 | 102.8 | 0.0 |
| 1 | 92.2 | (20.0) |
| 2 | 88.0 | (40.0) |
| 3 | 85.0 | (50.5) |
| 4 | 82.5 | (70.5) |
| 5 | 80.3 | — |
| 10 | 67.0 | (93.0) |
| 24 | 62.8 | 98.0 |

(*)The rate of dechlorination was given by measuring the chloride produced in the form of sodium chloride by the silver chloride gravimetric method.
The parenthesized figures were obtained by experiments repeated for each individual stage.

It was ascertained through gas chromatography and gas chromatography-mass spectrometry that the PCB had been converted into a large amount of biphenyl and a small amount of bicyclohexyl. In addition, it was ascertained by ignition test on the filter paper that the catalyst maintained its activity after the reaction was finished.

EXAMPLE 2

The hydrogenation-dechlorination reaction was carried out in the same manner as Example 1, except that the reaction temperature was 160° C. The relationship among the pressure of hydrogen in the autoclave, the rate of dechlorination and the reaction time are shown in Table 2:

TABLE 2

| REACTION TIME (minute) | TOTAL PRESSURE (mainly $H_2$) ($kg/cm^2$) | RATE OF DE-CHLORINATION (%) |
|---|---|---|
| 0 | 100.0 | 0.0 |
| 15 | 92.5 | (38.0) |
| 30 | 85.0 | (78.0) |
| 60 | 65.5 | (85.0) |
| 120 | 67.0 | 97.5 |

It was ascertained by ignition test on the filter paper that the catalyst maintained its activity after the reaction was finished.

EXAMPLE 3

The hydrogenation-dechlorination reaction was carried out in the same manner as Example 1, except that the reaction temperature was 200° C. The relationship among the pressure of hydrogen in the autoclave, the rate of dechlorination and the reaction time are shown in Table 3.

TABLE 3

| REACTION TIME (minute) | TOTAL PRESSURE (mainly $H_2$) ($kg/cm^2$) | RATE OF DE-CHLORINATION (%) |
|---|---|---|
| 0 | 100.0 | 0.0 |
| 5 | 92.0 | 50.0 |
| 20 | 80.2 | 82.5 |
| 40 | 60.0 | 91.5 |

It was ascertained by ignition test on the filter paper that the catalyst maintained its activity after the reaction was finished.

EXAMPLE 4

Instead of the isopropyl alcohol in EXAMPLE 1 20 ml of methyl alcohol was used to carry out the hydrogenation-dechlorination reaction. The relationship between the pressure of hydrogen in the autoclave and the reaction time is shown in Table 4.

TABLE 4

| REACTION TIME (hour) | TOTAL PRESSURE (mainly $H_2$) ($kg/cm^2$) |
|---|---|
| 0 | 133.5 |
| 1 | 124.5 |
| 2 | 114.5 |
| 3 | 107.0 |
| 4 | 97.5 |
| 5 | 90.5 |
| 6 | 90.0 |
| 24 | 89.0 |

After 24 hours it was found that the rate of dechlorination reached 87%, and it was ascertained by ignition test on the filter paper that the catalyst maintained its activity after the reaction was finished.

EXAMPLE 5

The hydrogenation-dechlorination reaction was carried out in the same manner as Example 1, except that 20 ml of acetone was added to the catalyst and total pressure of hydrogen was 70 $kgw/cm^2$. The reaction time, the pressure of hydrogen and the rate of dechlorination is shown in Table 5:

TABLE 5

Reaction temperature: 100° C.

| REACTION TIME (hour) | TOTAL PRESSURE (mainly $H_2$) ($kg/cm^2$) | RATE OF DE-CHLORINATION (%) |
|---|---|---|
| 0 | 70.5 | 0.0 |
| 0.25 | 51.5 | |
| 0.5 | 38.1 | |
| 1.0 | 34.0 | |
| 1.5 | 31.2 | |
| 2.0 | 27.2 | |
| 18.0 | 2.5 | |
| 19 | 2.4 | |
| 20 | 2.4 | 100.0 |

After the reaction the Raney nickel catalyst was found black and sludgy, and it was ascertained by ignition test on the filter paper that the catalyst was no longer active. It was also found through gas chromatography and gas chromatography-mass spectrometry that the PCB had been converted into biphenyl and bicyclohexyl, and that the acetone had been converted into isopropyl alcohol.

EXAMPLE 6

Instead of the acetone in Example 5, 20 ml of ethyl alcohol was used to carry out the hydrogenation-dechlorination reaction. The relationship among the reaction hour, the pressure of hydrogen and the rate of dechlorination is shown in Table 6:

TABLE 6

Reaction temperature: 100° C.

| REACTION TIME (hour) | TOTAL PRESSURE (mainly $H_2$) ($kg/cm^2$) | RATE OF DE-CHLORINATION (%) |
|---|---|---|
| 0 | 72.0 | 0.0 |
| 0.5 | 69.6 | |
| 1 | 67.7 | |
| 1.5 | 67.0 | |
| 2.0 | 66.2 | |
| 18 | 45.5 | |
| 19 | 45.4 | |

TABLE 6-continued

| Reaction temperature: 100° C. | | |
|---|---|---|
| REACTION TIME (hour) | TOTAL PRESSURE (mainly $H_2$) (kg/cm$^2$) | RATE OF DE-CHLORINATION (%) |
| 20 | 44.4 | 92.0 |

After the reaction was finished, it was ascertained by ignition test on the filter paper that the Raney nickel catalyst maintained its activity, and it was also ascertained through gas chromatography and gas chromatography-mass spectrometry that a great amount of biphenyl and a small amount of bicyclohexyl had been produced.

EXAMPLE 7

The hydrogenation dechlorination reaction was carried out, using a PCB having on average 3 chlorine atoms per molecule under 30 kgw/cm$^2$ total pressure of hydrogen but at various temperatures, namely 100° C., 160° C. and 200° C. In an autoclave 9 g of PCB (AC 1242) 20 ml of isopropyl alcohol, and 4.2 g of sodium hydroxide were mixed, and 10 g of a Raney nickel alloy powder (Ni: 40%) and about 74 ml of water were added thereto until the whole liquid phase containing the catalyst reached 100 ml. The Raney nickel alloy powder had been previously developed at 60° C. for 50 minutes in a 55 ml of 20% sodium hydroxide solution.

It was found that at temperatures of 160° and 200° C. the partial pressures of the dispersing agent (isopropyl alcohol) and water rose, and 150 ml of gaseous hydrogen was introduced into the autoclave so that the total pressure at each temperature could be maintained at 30 kg/cm$^2$ at the start of the reaction.

The relationship among the reaction time, the pressure of hydrogen and the rate of dechlorination for this Example 7 is shown in Tables 7, 8 and 9.

TABLE 7

| Reaction temperature: 100° C. | | |
|---|---|---|
| REACTION TIME (hour) | TOTAL PRESSURE (mainly $H_2$) (kg/cm$^2$) | RATE OF DE-CHLORINATION (%) |
| 0 | 32.0 | 0.0 |
| 1 | 25.5 | (31.2) |
| 2 | 22.5 | (53.6) |
| 3 | 19.0 | (50.6) |
| 4 | 15.2 | (80.3) |
| 5 | 11.8 | |
| 6 | 7.2 | (83.7) |
| 18 hour/25 min | 4.0 | 96.1 |

TABLE 8

| Reaction temperature: 160° C. | | |
|---|---|---|
| REACTION TIME (minute) | TOTAL PRESSURE (mainly $H_2$) (kg/cm$^2$) | RATE OF DE-CHLORINATION (%) |
| 0 | 26.4 | 0.0 |
| 5 | 22.0 | |
| 10 | 20.5 | |
| 15 | 19.0 | |
| 20 | 17.0 | |
| 25 | 15.0 | 61.2 |

TABLE 9

| Reaction temperature: 200° C. | | |
|---|---|---|
| REACTION TIME (minute) | TOTAL PRESSURE (mainly $H_2$) (kg/cm$^2$) | RATE OF DE-CHLORINATION (%) |
| 0 | 52.5 | 0.0 |
| 5 | 40.5 | 52.3 |

After the reaction was finished, it was found that the Raney nickel catalyst in the reaction at 100° C. maintained such an activity that it ignited as vigorously as before the reaction, when the same was cleansed with ethyl alcohol, and that the catalyst in the reaction at 160° C. ignited when the same was cleansed with acetone. On the other hand, the catalyst at 200° C. did not ignite even when the same was cleansed either with ethyl alcohol or acetone. It was ascertained through gas chromatograhy and gas chromatography-mass spectrometry that a great amount of biphenyl and a small amount of bicyclohexyl had been produced.

EXAMPLE 8

This experiment was effected with the use of a PCB having on average 4 chlorine atoms per molecule, at 100° C. under 30 kg/cm$^2$ total pressure (mainly gaseous hydrogen), the results of which are shown in Table 10. 7.65 g of PCB (produced by Kanegafuchi Kagaku Co., Ltd. KC-400) having 0.105 gram equivalent weight, 20 ml of isopropyl alcohol, and 4.2 g of sodium hydroxide (equivalent weight ratio to the PCB:1) were mixed in an autoclave. 10 g of a Raney nickol alloy powder (Ni:40%) was added together with water (about 63 ml) until the whole amount of the solution reached 100 ml. The Raney nickel alloy powder had been previously developed at 60° C. for 50 minutes in 55 ml of a 20% solution of sodium hydroxide. Then gaseous hydrogen was introduced into the autoclave in an amount sufficient to secure a total pressure of 30 kb/cm$^2$. The relationships are shown in Table 10:

TABLE 10

| Reaction temperature: 100° C. | | |
|---|---|---|
| REACTION TIME (hour) | TOTAL PRESSURE (mainly $H_2$) (kg/cm$^2$) | RATE OF DE-CHLORINATION (%) |
| 0 | 31.2 | 0.0 |
| 0.5 | 25.2 | |
| 1 | 21.2 | |
| 1.5 | 17.4 | |
| 2 | 14.0 | |
| 2.5 | 11.3 | |
| 3 | 8.2 | 98.5 |

Twenty-four hours after the reaction was finished, it was found by ignition test that the Raney nickel catalyst showed the same igniting ability as before the reaction, which demonstrated that it maintained its catalytic activity. In addition, it was ascertained through gas chromatography and gas chromatography-mass specrometry that a great amount of biphenyl and a small amount of bicyclohexyl had been produced.

COMPARATIVE TEST (1)

The reaction was carried out in the same manner as Example 8, except that no alkali was used. The relationship among the reaction hour, the total pressure of hydrogen and the rate of dechlorination is shown in Table II:

TABLE 11

| REACTION TIME (hour) | TOTALY PRESSURE (mainly $H_2$) (kg/cm$^2$) | RATE OF DE-CHLORINATION (%) |
|---|---|---|
| 0 | 34.2 | 0.0 |
| 0.5 | 34.3 | |
| 1 | 33.6 | |
| 1.5 | 33.3 | |
| 2 | 33.0 | |
| 2.5 | 32.7 | |
| 3 | 32.6 | 15.0 |

After the reaction was finished it was found that pH had changed to about 5.5. The catalyst was found black and sludgy, and ignition test did not show that the catalyst maintained its activity. This shows that without alkali, the catalytic activity does not last thereby resulting in a short reaction life.

COMPARATIVE TEST (2)

A hydrogenation-dechlorination reaction was effected in the same manner as Example 8 except that no emulsifying dispersing agent was used. The relationship among the reaction hour, the total pressure of hydrogen, and the rate of dechlorination is shown in Table 12:

TABLE 12

| REACTION TIME (hour) | TOTAL PRESSURE (mainly $H_2$) (kg/cm$^2$) | RATE OF DE-CHLORINATION (%) |
|---|---|---|
| 0 | 31.3 | 0.0 |
| 0.5 | 32.1 | |
| 1 | 32.1 | |
| 1.5 | 32.1 | |
| 2 | 32.1 | |
| 2.5 | 32.1 | |
| 3 | 32.1 | 1.26 |

No pressure drop was observed, but it was found by ignition test that the catalyst maintained its activity after the reaction was finished. This test shows that without the use of an emulsifying dispersing agent the reaction cannot be effectively developed.

COMPARATIVE TEST (3)

The hydrogenation-dechlorination reaction was effected in the same manner as Example 8, except that a standard emulsifying agent, an anionic surfactant (specifically n-dodecylbenzene sulfonic acid) was used rather than a low molecular weight alcohol. The results are shown in Table 13:

TABLE 13

| Reaction Temperature: 100° C. | | |
|---|---|---|
| REACTION TIME (Hour) | TOTAL PRESSURE (mainly $H_2$) (kg/cm$^2$) | RATE OF DE-CHLORINATION |
| 0 | 75.0 | 0.0 |
| 6 | 75.0 | 0.0 |
| 12 | 74.9 | 0.0 |
| 18 | 74.8 | 0.0 |

This test shows that the emulsifying-dispersing agent cannot be just any surfactant but must be a low molecular weight alcohol.

EXAMPLE 9

The hydrogenation-dechlorination reaction was effected in the same manner as Example 8, except for the use of a PCB having on average 5 chlorine atoms per molecule 6.80 g (0.105 gram equivalent weight) of the PCB was used. The results are shown in Table 14.

TABLE 14

| Reaction temperature: 100° C. | | |
|---|---|---|
| REACTION TIME (hour) | TOTAL PRESSURE (mainly $H_2$) (kg/cm$^2$) | RATE OF DE-CHLORINATION (%) |
| 0 | 30.9 | 0.0 |
| 0.5 | 26.0 | |
| 1 | 22.2 | |
| 1.5 | 20.0 | |
| 2 | 18.0 | |
| 2.5 | 16.0 | |
| 3 | 15.3 | 83.7 |

Twenty-four hours after the reaction was finished, an ignition test was conducted upon the Raney nickel catalyst and it was found that it ignited in the same manner as before the reaction, which shows that its catalytic activity was maintained after the reaction. In addition, it was ascertained through gas chromatography and gas chromatography-mass spectrometry that a great amount of biphenyl and a small amount of bicyclohexyl had been produced.

EXAMPLE 10

The hydrogenation-dechlorination reaction was effected in the same manner as Example 8, except for the use of a PCB having on average 6 chlorine atoms per molecule 6.29 g (0.105 gram equivalent weight) of the PCB was used. The results are shown in Table 15:

TABLE 15

| Reaction temperature: 100° C. | | |
|---|---|---|
| REACTION TIME (hour) | TOTAL PRESSURE (mainly $H_2$) (kg/cm$^2$) | RATE OF DE-CHLORINATION (%) |
| 0 | 31.4 | 0.0 |
| 0.5 | 31.0 | |
| 1 | 27.3 | |
| 1.5 | 25.0 | |
| 2 | 22.5 | |
| 2.5 | 20.2 | |
| 3 | 17.9 | 74.45 |

Twenty-four hours after the reaction was finished, it was found by ignition test that the catalyst maintained its activity. It was ascertained through chromatography and gas chromatography-mass spectrometry that a great amount of biphenyl and a small amount of bicyclohexyl had been produced.

EXAMPLE 11

The hydrogenation-dechlorination reactions of Example 8 were effected, using a PCB having on average 10 chlorine atoms per molecule at 160° C., with 40 ml of isopropyl alcohol. The results of this reaction are shown in Table 16.

TABLE 16

| Reaction temperature: 160° C. | | |
|---|---|---|
| REACTION TIME (hour) | TOTAL PRESSURE (mainly $H_2$) (kg/cm$^2$) | RATE OF DE-CHLORINATION (%) |
| 0 | 28.5 | 0.0 |
| 0.5 | 26.9 | |
| 1 | 23.7 | |
| 1.5 | 21.2 | |
| 2 | 19.9 | |
| 2.5 | 18.9 | |

TABLE 16-continued

| Reaction temperature: 160° C. | | |
|---|---|---|
| REACTION TIME (hour) | TOTAL PRESSURE (mainly $H_2$) ($kg/cm^2$) | RATE OF DE-CHLORINATION (%) |
| 3 | 18.7 | 82.66 |

After the reaction was finished, it was found that the Raney nickel catalyst had been reduced in size to grains of 1 to 3 mm, and after the same was cleansed with ethyl alcohol, ignition test showed that it maintained its catalytic activity though it was slightly lowered. It has also been ascertained through gas chromatography and gas chromatography-mass spectrometry that a great amount of biphenyl and a small amount of bicyclohexyl had been produced.

EXAMPLE 12

Instead of the Raney nickel catalyst of Example 8 250 mg of carbon supported palladium catalyst (10%) was used to effect the hydrogenation-dechlorination reaction. The reaction was continued for a total of two and one-half hours. The results are shown in Table 17:

TABLE 17

| Reaction temperature: 100° C. | | |
|---|---|---|
| REACTION TIME (hour) | TOTAL PRESSURE mainly $H_2$ ($kg/cm^2$) | RATE OF DE-CHLORINATION (%) |
| 0 | 30.5 | 0.0 |
| 0.25 | 12.9 | |
| 0.5 | 11.2 | |
| 1.0 | 9.6 | |
| 1.5 | 8.2 | |
| 2.0 | 7.2 | |
| 2.5 | 6.4 | 100.0 |

It was ascertained through gas chromatography and gas chromatography-mass spectrometry that the PCB had been converted into a great amount of biphenyl and a small amount of bicyclohexyl.

EXAMPLE 13

7.65 g of PCB (KC-44) having on average 4 chlorine atoms per molecule (0.105 gram equivalent weight), 6.18 g of potassium hydroxide (0.105 gram equivalent weight), and 30 ml of ethyl alcohol (as a dispersing agent) were mixed, and the hydrogenation-dechlorination reaction was effected under a 30 $kgw/cm^2$ total pressure of hydrogen and with 100 mg of a carbon-supported palladium catalyst (10%). The reaction was carried out at 100° C. for two and one-half hours, the results of which are shown in Table 18:

TABLE 18

| REACTION TIME (hour) | TOTAL PRESSURE (mainly $H_2$) ($kg/cm^2$) | RATE OF DE-CHLORINATION (%) |
|---|---|---|
| 0 | 29.9 | 0.0 |
| 0.25 | 25.3 | |
| 0.5 | 20.1 | |
| 1 | 16.9 | |
| 1.5 | 16.4 | |
| 2 | 16.1 | |
| 2.5 | 15.9 | 86.0 |

It was found through gas chromatography and gas chromatography-mass spectrometry that the products contained a great amount of biphenyl and a small amount of bicyclohexyl.

EXAMPLE 14

The hydrogenation-dechlorination reaction was effected in the same manner as Example 8, except for the use of 500 mg of 5% platinum on carbon as a catalyst, the results of which are shown in Table 19:

TABLE 19

| REACTION TIME (hour) | TOTAL PRESSURE (mainly $H_2$) ($kg/cm^2$) | RATE OF DE-CHLORINATION (%) |
|---|---|---|
| 0 | 32.8 | 0.0 |
| 0.5 | 31.9 | |
| 1 | 30.8 | |
| 1.5 | 30.0 | |
| 2 | 29.1 | |
| 2.5 | 28.2 | |
| 3 | 27.2 | 25.4 |

It was found through gas chromatography and gas chromatography-mass spectrometry that the products contained a great amount of biphenyl and a small amount of bicyclohexyl.

In the following Examples 15 and 16, reference is made to the accompanying drawings wherein.

EXAMPLE 15

Figure 1:
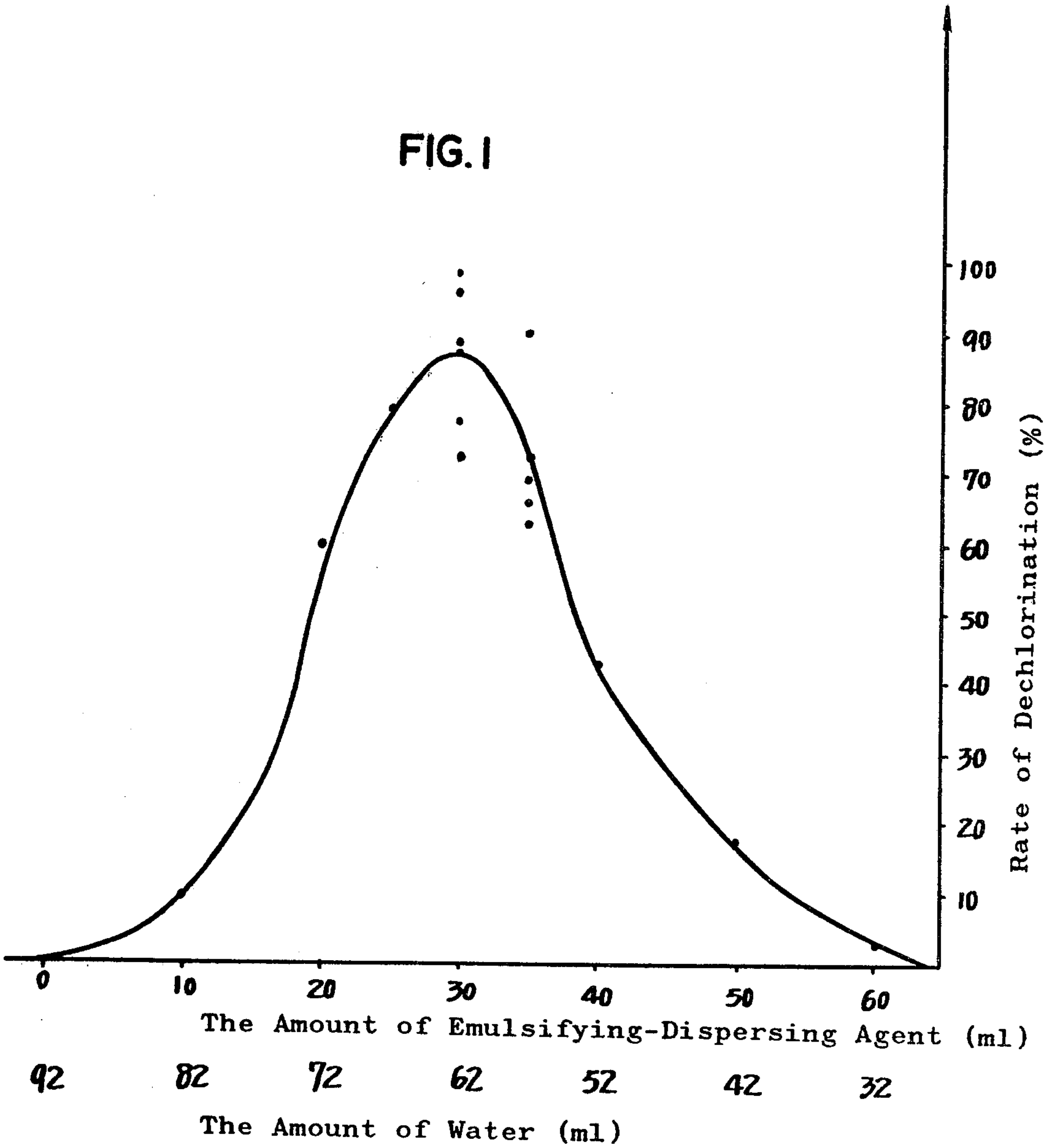
FIG. 1 is a graph depicting the relationship between the rate of dechlorination and the amount of emulsifying-dispersing agent in a hydrogenation-dechlorination reaction of PCB having 4 chlorides (reaction temperature: 100° C., reaction hour: 3 hrs)

This experiment is a modification to Example 8 in which the mixing ratio of isopropyl alcohol and water was changed. The results are depicted by the graph in FIG. 1. It was found that with the use of 10 ml of isopropyl alcohol, the decomposition rate was not sufficient irrespective of the remaining catalytic activity. Even in the case of a PCB having on average 3 chlorine atoms per molecule, the decomposition rate did not remarkably improve during the 3 hour reaction. When the dispersing agent is added in an amount greater than water (exceeding 50 ml), the decomposition rate became worse. When it amounted to 70 ml, only alkaline decomposition occurred, after which the PCB was found slightly brown.

EXAMPLE 16

Figure 2:
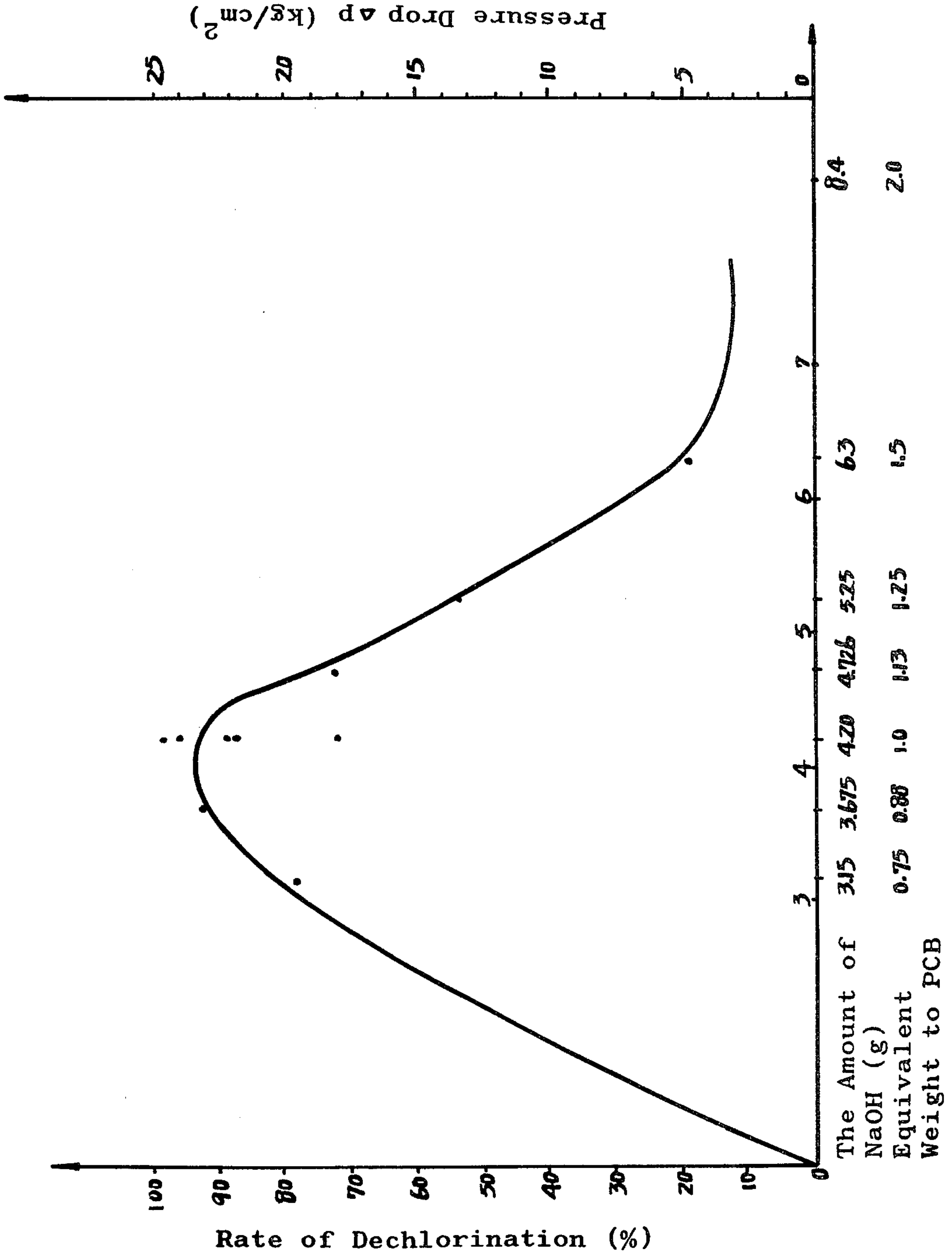
FIG. 2 is a graph depicting the relationship among the amount of sodium hydroxide, the rate of dechlorination and pressure drop (the emulsifying-dispersing agent: isopropyl alcohol; reaction temperature: 100° C.; reaction time three hours).

In this experiment the amount of sodium hydroxide in Example 8 was variously changed, the results of which are depicted by the graph in FIG. 2.

The graph shows that the decomposition rate in the range of 0.75 to 1.25 equivalent weight ratio to PCB is better than in other ranges. Under the conditions of Example 8, when the ratio of sodium hydroxide equivalent weight to PCB equivalent weight is not greater than 1, the rate of dechlorination is almost equal to the ratio of equivalent weight. From this it will be appreciated that the reaction accelerates in the zone ranging from the point of neutralization to the acid zone. In this case, after the reaction is finished, the catalyst loses its activity.

When the ratio is greater than 1, the rate of dechlorination becomes progressively worse; when it is up to 1.25 the rate of dechlorination still exceeds 50%, but when the ratio is greater than 1.25, it adversely affects the reaction. The catalytic activity is still maintained, however, when the ratio of sodium hydroxide equivalent weight to PCB equivalent weight ranges from 1 to 2.

In a mixture of water and isopropyl alcohol (mixing ratio: about 2 to 1) the optimum concentration of sodium hydroxide is about 1 N. It is to be understood that this is a balancing of the good dispersion obtained at below 1 N with the good reaction obtained at above 1 N.

What is claimed is:

1. A method of treating polychlorinated biphenyl compounds in aqueous solution to render them substantially harmless, said method comprising:

(A) admixing with said polychlorinated biphenyl compounds the following ingredients with respect to each one gram of chlorine atoms contained in said polychlorinated biphenyl compounds;
  (a) from 400 to 2000 ml of water;
  (b) from 0.5 to 1.25 gram equivalent weight of an alkali material selected from those metal hydroxides capable of reacting with hydrogen chloride to form a salt;
  (c) from 100 to 450 ml of an emulsifying-dispersing agent selected from the group consisting of low molecular weight alcohols;
  (d) a hydrogenation catalyst in an effective amount to promote the reaction between hydrogen and said polychlorinated biphenyl compounds;

(B) maintaining said admixture within a pressure range of normal to 100 atmospheres and within a temperature range not higher than 200° C. and, while it is so maintained, introducing gaseous hydrogen in an amount greater than that calculated to be necessary to react with all the chlorines present in the polychlorinated biphenyl compounds.

2. A method of disposing of polychlorinated biphenyls as claimed in claim 1, wherein the amount of said water ranges from 900 ml to 1200 ml, the alkali from 0.75 to 1.1 gram equivalent weight, and the alcohol from 170 ml to 380 ml, with respect to chlorine of 1.0 gram equivalent weight contained in said polychlorinated biphenyls.

3. A method as claimed in claim 1 in which said treatment of polychlorinated biphenyl compounds is performed at a temperature not higher than 200° C. under a pressure of normal to 100 atm.

4. A method as claimed in claim 1 in which said treatment of polychlorinated biphenyl compounds is performed at a temperature of 40° to 160° under a pressure of normal to 30 atm.

5. A method as claimed in claim 1 in which said alkali material is sodium hydroxide.

6. A method as claimed in claim 1 in which said alkali material is potassium hydroxide.

7. A method as claimed in claim 1 in which said emulsifying-dispersing agent is methyl alcohol.

8. A method as claimed in claim 1 in which said emulsifying-dispersing agent is ethyl alcohol.

9. A method as claimed in claim 1 in which said emulsifying-dispersing agent is isopropyl alcohol.

10. A method as claimed in claim 1 in which said hydrogenation catalyst is a Raney nickel catalyst.

11. A method as claimed in claim 1 in which said hydrogenation catalyst is a carbon-supported palladium catalyst.

12. A method of treating polychlorinated biphenyl compounds in aqueous solution to render them substantially harmless, said method comprising:

(A) admixing in an aqueous medium
  (a) said polychlorinated biphenyl compounds to be treated;
  (b) an emulsifying-dispersing agent which is a low molecular weight alcohol and which is effective to and present in sufficient amount to emulsify and disperse said polychlorinated biphenyl compounds;
  (c) strongly basic alkali material capable of reacting with hydrogen chloride to form a salt, said alkali material being present in sufficient amount to react with all hydrogen chloride formed;
  (d) a hydrogenation catalyst in an amount effective to promote the reaction between hydrogen and said polychlorinated biphenyl compounds;

(B) introducing gaseous hydrogen to said admixture, hydrogen being introduced in a greater amount than the calculated amount necessary to react with all the chlorines present in the polychlorinated biphenyl compounds.

* * * * *